United States Patent [19]

Manzer

[11] Patent Number: 4,922,037

[45] Date of Patent: May 1, 1990

[54] GAS-PHASE FLUORINATION PROCESS

[75] Inventor: Leo E. Manzer, Wilmington, Del.

[73] Assignee: E. I. du Pont de Nemours and Company, Wilmington, Del.

[21] Appl. No.: 355,867

[22] Filed: May 19, 1989

Related U.S. Application Data

[63] Continuation of Ser. No. 160,003, Feb. 24, 1988, abandoned.

[51] Int. Cl.$^5$ .................. C07C 17/20; C07C 19/02
[52] U.S. Cl. .................................... 570/168; 570/166
[58] Field of Search .............................. 570/168, 166

[56] References Cited

U.S. PATENT DOCUMENTS

| | | | |
|---|---|---|---|
| 2,005,707 | 6/1935 | Daudt et al. | 570/168 |
| 2,744,147 | 5/1956 | Milks | 260/653 |
| 2,744,148 | 5/1956 | Ruh et al. | 260/653 |
| 3,650,987 | 3/1972 | Vecchio et al. | 570/166 |
| 3,787,331 | 1/1974 | Groppelli et al. | 570/166 |
| 3,793,229 | 2/1974 | Groppelli et al. | 570/166 |
| 4,129,603 | 12/1978 | Bell | 260/653 |
| 4,158,675 | 6/1979 | Potter | 260/653.7 |

FOREIGN PATENT DOCUMENTS

| | | | |
|---|---|---|---|
| 27138 | 2/1980 | Japan . | |
| 8234 | 1/1985 | Japan | 570/168 |
| 2030981 | 4/1980 | United Kingdom . | |

*Primary Examiner*—J. E. Evans
*Attorney, Agent, or Firm*—James E. Shipley

[57] ABSTRACT

An improved process for the manufacture of 1,1,1,2-tetrafluoroethane, more particularly, a gas-phase reaction of a 1,1,1-trifluorochloroethane with hydrogen fluoride in the presence of a selected metal on aluminum fluoride or carbon.

13 Claims, No Drawings

GAS-PHASE FLUORINATION PROCESS

This application is a continuation Ser. No. 07/160,003 filed Feb. 24, 1988, now abandoned.

FIELD OF THE INVENTION

An improved process for the manufacture of 1,1,1,2-tetrafluoroethane, more particularly, a gas-phase reaction of 1,1,1-trifluorochloroethane with hydrogen fluoride in the presence of a selected metal on aluminum fluoride or carbon.

BACKGROUND OF THE INVENTION

U.S. Pat. No. 2,744,147 discloses an alumina catalyst which may be promoted with a metal (cobalt, nickel and chromium) and a process using the catalyst in a fluidized bed for fluorinating haloalkanes at a temperature between 180° to 425° C. Haloalkanes which are disclosed which are suitable for fluorination include carbon tetrachloride, chloroform, 1,1,1-trichloroethane, methylene chloride, 1,1-dichloroethane, 1,1,2-trichloroethane, uns. tetrachloroethane, methylene bromide, bromoform, carbon tetrabromide, acetylene tetrabromide, dichlorofluoromethane, dichlorodifluoromethane, dibromodichloromethane and bromochlorodifluoromethane.

U.S. Pat. No. 2,744,148 discloses an alumina catalyst which may be promoted with a metal (chromium, cobalt, nickel, copper and palladium) and a process for fluorinating haloalkanes to highly fluorinated products. A process is disclosed which activates the catalyst and converts at least part of the alumina to basic aluminum fluorides.

U.S. Pat. No. 4,129,603 discloses and claims a process for the manufacture of 1,1,1,2-tetrafluoroethane which comprises reacting, in the vapor phase at elevated temperature, a haloethane of formula $CX_3CH_2Y$ wherein X is bromine, chlorine or fluorine and Y is chlorine with hydrogen fluoride in the presence of a catalyst which is chromium (III) oxide or which is at least in part basic chromium (III) fluoride, and wherein the 1,1,1,2-tetrafluoroethane product contains 1,1-difluoro-2-chloroethylene as an undesirable impurity which is removed by intimate contact with a metal permanganate in a liquid medium. The impurity is difficult to remove from the product stream and requires additional capital investment to separate; in addition, the impurity leads to catalyst deactivation.

U.S. Pat. No. 4,158,675 discloses and claims a process for the manufacture of 1,1,1,2-tetrafluoroethane which comprises reacting, in the vapor phase at elevated temperature, a haloethane of formula $CX_3CH_2Y$ wherein X is bromine, chlorine or fluorine and Y is chlorine with hydrogen fluoride in the presence of a catalyst which is chromium (III) oxide or which is, at least in part, basic chromium (III) fluoride, and wherein the 1,1,1,2-tetrafluoroethane product containing 1,1-difluoro-2-chloroethylene as impurity is brought together with hydrogen fluoride into contact with said catalyst which is chromium (III) oxide or which is at least in part basic chromium (III) fluoride at a temperature in the range 100° C. to 275° C. to reduce the amount of the impurity.

JP 55/27138 discloses and claims a process for the manufacture of 1,1,1,2-tetrafluoroethane which comprises reacting 1,1,1-trifluorochloroethane and hydrogen fluoride at a molar ratio of 1:3–20 in the presence of inorganic chromium (III) compounds at 300°–450° C. The preferred molar ratio of 1,1,1-trifluorochloroethane to hydrogen fluoride is 1:5–20. The reaction temperature is 350°–420° C. The reaction pressure is atmospheric pressure to 10 kg/cm$^2$G, and the reaction time is 1–30 seconds. The selectivity to 1,1,1,2-tetrafluoroethane is high at high conversion. Chromium (III) compounds which are suitable for the reaction include the oxide, hydroxide, halide such as chloride, bromide, iodide and fluoride, and inorganic acid salts such as sulphate, nitrate, carbonate and phosphate. The chromium compound is pretreated at reaction conditions of temperature and pressure under an atmosphere of hydrogen fluoride for 1–5 hours to stabilize the activity.

In the above process a mole ratio of hydrogen fluoride/1,1,1-trifluorochloroethane of 1:1 produces 1-chloro-2,2-difluoroethylene as the major by-product. If the mole ratio is above 5:1 the selectivity to 1,1,1,2-tetrafluoroethane exceeds 95%. The conversion is negligible at 200° C., but it reaches 20% above 350° C. The conversion increases with temperature, but the selectivity decreases. Below 420° C., the selectivity is above 95% at the mole ratio of 8:1, and it is above 90% below 450° C.

GB 2,030,981 discloses the preparation of 1,1,1,2-tetrafluoroethane by reaction of 1,1,1-trifluorochloroethane with HF in the presence of an inorganic chromium (III) compound, in which 0.002–0.05 moles of oxygen per mole of 1,1,1-trifluorochloroethane is passed into the reaction system. The molar ratio of HF to 1,1,1-trifluorochloroethane is preferably 3–20:1; most preferably 5–12:1. Reaction temperature is 300°–450° C., most preferably 350°–420° C. and the reaction time is 1–30 seconds. The catalyst is chromium (III) oxyfluoride, oxide, hydroxide, halide, inorganic acid salt, or their hydrates. The high and selective conversion by the catalyst is maintained by addition of oxygen and loss of catalytic activity is retarded.

It is an object of this invention to prepare 1,1,1,2-tetrafluoroethane via fluorination of 1,1,1-trifluorochloroethane with HF in the presence of non-chromium catalysts. Additional objects are to provide a catalyst which can either maintain a high degree of activity and selectivity in the absence of oxygen (metals supported on aluminum fluoride) or can substantially prevent the formation of $CF_2=CHCl$ (metals supported on carbon).

SUMMARY OF THE INVENTION

What has been discovered is a process for the preparation of 1,1,1,2-tetrafluoroethane by fluorination of 1,1,1-trifluorochloroethane, which process comprises contacting in the gaseous phase at about 300° C. to about 500° C. said 1,1,1-trifluorochloroethane with HF and a catalyst comprising at least one metal, said metal selected from a group consisting of a metal from Groups VIII, VIIB, IIIB, IB and/or a metal having an atomic number of 58 through 71, said metal on aluminum fluoride or carbon, said metal having an oxidation state greater than zero, said contacting producing a product stream containing 1,1,1,2-tetrafluoroethane and, thereafter, separating the 1,1,1,2-tetrafluoroethane from the product stream.

Metals on aluminum fluoride have unusually long lifetimes and high selectivities for this process as compared to unsupported chromium (III) compounds.

Metals on carbon produce substantially no $CF_2=CHCl$.

DETAILS OF THE INVENTION

The invention catalyst can be prepared in any manner known to the art. For example, the invention catalyst can be prepared by fluorination of alumina or carbon impregnated with a solution of at least one metal from Groups VIII (iron, cobalt, nickel, ruthenium, rhodium, palladium, osmium, iridium, platinum), VIIB (manganese, technetium, rhenium), IIIB (scandium, yttrium, lanthanum). IB (copper, silver, gold), and/or a metal having an atomic number of 58 through 71 (cerium, praseodymium, neodymium, promethium, samarium, europium, gadolinium, terbium, dysprosium, holmium, erbium, thulium, ytterbium or lutetium), which is in the form of a soluble compound of the metal such as the oxide, oxyhalide, halide, pseudohalide, nitrate, phosphate, carbonate, sulfate or organic acid salts such as acetates, propionates and any other compound of said metals which is convertible to a metal fluoride under the reaction conditions or catalyst pretreatment conditions described herein. The halides include fluorides, chlorides and bromides. The pseudohalides include cyanides, cyanates and thiocyanates. The preferred metals are cobalt, lanthanum, nickel, and manganese. The most preferred metal is cobalt.

In addition, when it is desired that the metal be on aluminum fluoride, the invention catalyst can also be prepared by co-precipitation of the catalytic metal and the aluminum as the hydroxides which are thereafter dried and calcined to form the mixed oxides, a technique well known to the art. The resulting oxide can be fluorinated as described herein.

The total content of metal on carbon or alumina should be a catalytically effective amount and, expressed as the metal, is generally not more than 50% by weight of the catalyst and preferably not more than 20% by weight of the catalyst, and usually at least 0.02% by weight of the catalyst. A more preferred range is 0.1 to 10% by weight of the catalyst.

The form of the catalyst is not critical and may be used in the form of pellets, powders or granules.

The alumina is converted to aluminum fluoride under the conditions of fluorination as described herein.

The reaction of the 1,1,1-trifluorochloroethane with HF in the presence of the catalyst composition of the instant invention is conducted at about 300° C. to 500° C., preferably about 350° C. to 475° C. and most preferably about 400° C. to 450° C.

The contact time can vary widely depending on the degree of conversion desired and generally will be about 0.1 to 60 seconds, preferably about 10 to 30 seconds.

The amount of HF should be at least a stoichiometric amount. Generally, the molar ratio of HF to 1,1,1-trifluorochloroethane can range from about 3/1 to 30/1, preferably about 3/1 to 20/1 and more preferably about 5/1 to 10/1.

During the course of the reaction, unreacted 1,1,1-trifluorochloroethane can be recycled.

The reaction of 1,1,1-trifluorochloroethane with HF may be conducted in any suitable reactor, including fixed and fluidized bed reactors. The reaction vessel should be constructed from materials which are resistant to the corrosive effects of hydrogen fluoride and water such as "Hastelloy" and "Inconel".

Generally, the catalyst composition of the present invention will be pretreated with HF or other vaporizable compounds containing fluorine such as $CCl_3F$, $ScF_4$, $CCl_2F_2$, $CHF_3$, or $CCl_2FCClF_2$ to activate the catalyst. This pretreatment is accomplished by placing the catalyst composition in a suitable container which can be the reactor to be used to perform the reaction of the instant invention, and thereafter, passing HF over the dried catalyst composition. This is conveniently carried out by passing HF over the catalyst for a period of time, for example, of about 15 to 300 minutes at a temperature of, for example, about 200° C. to about 450° C. Nevertheless, this pretreatment is not essential; initial process conditions and equipment could be selected so as to activate the catalyst under initial process conditions.

Pressure is not critical. Atmospheric and superatmospheric pressures are the most convenient and are therefore preferred.

The metals of the instant invention on aluminum fluoride have unusually long lifetimes and selectivities as compared to catalysts disclosed in the literature.

It has been discovered that the metals of this invention when supported on carbon have high selectivities and produce a product stream which contains substantially no $CF_2=CHCl$. By substantially no $CF_2=CHCl$ is meant that the product stream contains less than or equal to 0.01% $CF_2=CHCl$.

1,1,1,2-Tetrafluoroethane produced by the invention has utility as a refrigerant, blowing agent, dispersant gas for aerosol sprays, sterilant gas, etc.

EXAMPLES

In the following illustrative Examples, all parts and percentages are by weight and all temperatures are Centigrade. All reactions used commercial HF containing only trace amounts of water. All product compositions are given in area percents and selectivities are calculated based on area percents.

General Procedure for Fluorination

The reactor (a 0.5 inch ID, 12 inch long "Inconel" pipe) was charged with the amount of catalyst as described in the following examples, and placed in a sand bath. The bath was gradually heated to 400° while dry nitrogen gas at a flow rate of 50 ml/minute was passed through the reactor to remove traces of water. The temperature was lowered and maintained at about 200° while HF and nitrogen gas (1:4 molar ratio) were passed through the reactor and the nitrogen flow was decreased with time until neat HF was being passed through the reactor. At this point, the temperature was gradually raised to 450° and maintained there for 15 to 300 minutes. X-ray diffraction analysis showed that when alumina was used, it was converted to essentially all aluminum fluoride.

While maintaining HF flow, the temperature was then adjusted to the indicated values and, thereafter, 1,1,1-trifluorochloroethane flow was started. The flows of HF and 1,1,1-trifluorochloroethane were adjusted to give the indicated molar ratio and contact times in the Examples.

The reactor effluent was scrubbed with aqueous potassium hydroxide to remove HCl and HF and sampled on-line with a Hewlett Packard HP 5890 gas chromatograph using a 20 foot long, one-eighth inch diameter, column containing "Krytox" perfluorinated polyether on an inert support and a helium flow of 35 cc/minute. Gas chromatographic conditions were 70° for 3 minutes followed by temperature programming to 180° at a rate of 6°/minute.

EXAMPLE 1

The General Procedure for Fluorination was followed using 19.1 g (30 cc) of $CoCl_2/Al_2O_3$ (2.0% Co) in the form of extrudates one-twentieth inch diameter. The reaction temperature was 410° C., the ratio of $HF/CF_3CH_2Cl$ was 10/1 and the contact time was 30 seconds. The results of the reaction of HF with $CF_3CH_2Cl$ over the prepared catalyst are given in Table 1.

TABLE 1

| Hrs. | $CF_3CH_2Cl$ Conversion | $CF_3CH_2F$ Selectivity |
|---|---|---|
| 5 | 34.7% | 93.4% |
| 10 | 34.1% | 93.0% |
| 15 | 34.7% | 93.4% |
| 20 | 33.5% | 93.1% |
| 25 | 32.8% | 93.0% |
| 30 | 33.0% | 93.6% |
| 38 | 33.1% | 94.0% |

The activity of the catalyst showed a 4.6% deterioration in 38 hours.

By comparison, Comparative Example 1 in GB 2,030,981 in which unsupported chromium (III) was used as the catalyst with a $HF/CF_3CH_2Cl$ of 7.7/1 at a temperature of 400° C. showed a 7.7% deterioration of the catalyst after 29 hours and a 15.4% deterioration of the catalyst after 44 hours.

EXAMPLE 2

The General Procedure for Fluorination was followed using 19.1 g (30 cc) of $CoCl_2/Al_2O_3$ (2.0% Co) in the form of extrudates one-twentieth inch diameter. The reaction temperature was 450° C., the ratio of $HF/CF_3CH_2Cl$ was 20/1 and the contact time was 30 seconds. The results of the reaction of HF with $CF_3CH_2Cl$ over the prepared catalyst are given in Table 2.

TABLE 2

| Hrs. | $CF_3CH_2Cl$ Conversion | $CF_3CH_2F$ Selectivity |
|---|---|---|
| 5 | 50.3% | 83.9% |
| 10 | 49.5% | 83.6% |
| 15 | 48.6% | 82.9% |
| 20 | 47.5% | 83.2% |
| 21 | 47.2% | 83.3% |

The activity of the catalyst shows a 6.2% deterioration in 21 hours.

EXAMPLE 3

The General Procedure for Fluorination was followed using 18.9 g (30 cc) of $CoCl_2/Al_2O_3$ (0.1% Co.) in the form of extrudates one-twentieth inch diameter. The results of the reaction of HF with $CF_3CH_2Cl$ over the prepared catalyst at 450° C. are given in Table 3.

TABLE 3

| Ex. | $HF/CF_3CH_2Cl$ | C.T. (Sec) | $CF_3CH_2Cl$ | $CF_3CH_2F$ | Other |
|---|---|---|---|---|---|
| 2 | 20/1 | 30 | 56.5% | 34.4% | 9.1% |

EXAMPLE 4

The General Procedure for Fluorination was followed using 26.4 g (30 cc) of $CoCl_2/Al_2O_3$ (20% Co) in the form of extrudates one-twentieth inch diameter. The results of the reaction of HF with $CF_3CH_2Cl$ over the prepared catalyst at 450° C. are given in Table 4.

TABLE 4

| Ex. | $HF/CF_3CH_2Cl$ | C.T. (Sec) | $CF_3CH_2Cl$ | $CF_3CH_2F$ | Other |
|---|---|---|---|---|---|
| 4 | 20/1 | 30 | 64.5% | 30.2% | 5.3% |

EXAMPLES 5-7

The General Procedure for Fluorination was followed using 19.8 g (30 cc) of $NiCl_2/Al_2O_3$ (2% Ni) in the form of extrudates one-twentieth inch diameter. The results of the reaction of HF with $CF_3CH_2Cl$ over the prepared catalyst with a contact time of 30 seconds are given in Table 5-7.

TABLE 5-7

| Ex. | Temp. | $HF/CF_3CH_2Cl$ | $CF_3CH_2Cl$ | $CF_3CH_2F$ | Other |
|---|---|---|---|---|---|
| 5 | 350° | 10/1 | 92.0% | 6.9% | 1.1% |
| 6 | 400° | 10/1 | 78.0% | 18.7% | 3.3% |
| 7 | 425° | 10/1 | 68.0% | 27.4% | 4.6% |

EXAMPLE 8

The General Procedure for Fluorination was followed using 20.7 g (30 cc) of $MnCl_2/Al_2O_3$ (3.6% Mn) in the form of extrudates one-twentieth inch diameter. The results of the reaction of HF with $CF_3CH_2Cl$ over the prepared catalyst at 450° C. are given in Table 8.

TABLE 8

| Ex. | $HF/CF_3CH_2Cl$ | C.T. (sec.) | $CF_3CH_2Cl$ | $CF_3CH_2F$ | Other |
|---|---|---|---|---|---|
| 8 | 20/1 | 30 | 84.4% | 9.8% | 5.8% |

EXAMPLES 9-11

The General Procedure for Fluorination was followed using 20.2 g (30 cc) of $RuCl_4/Al_2O_3$ (2% Ru) in the form of extrudates one-twentieth inch diameter. The results of the reaction of HF with $CF_3CH_2Cl$ over the prepared catalyst with a 30 second contact time are given in Table 9-11.

TABLE 9-11

| Ex. | Temp. | $HF/CF_3CH_2Cl$ | $CF_3CH_2Cl$ | $CF_3CH_2F$ | Other |
|---|---|---|---|---|---|
| 9 | 350° | 20/1 | 69.7% | 29.9% | 0.4% |
| 10 | 400° | 20/1 | 59.4% | 38.0% | 2.6% |
| 11 | 450° | 20/1 | 53.9% | 39.6% | 6.5% |

EXAMPLES 12-15

The General Procedure for Fluorination was followed using 12.75 g (15 cc) of $LaCl_3/C$ (22.6% La) in the form of granules. The results of the reaction of HF with $CF_3CH_2Cl$ over the prepared catalyst are given in Table 12-15. Examples 12 and 13 were conducted at 400° C. and Examples 14 and 15 were conducted at 450° C.

TABLE 12-15

| Ex. | $HF/CF_3CH_2Cl$ | C.T. (sec.) | $CF_3CH_2Cl$ | $CF_3CH_2F$ | Other |
|---|---|---|---|---|---|
| 12 | 20/1 | 5 | 92% | 7% | 1% |
| 13 | 20/1 | 10 | 87% | 12% | 1% |
| 14 | 10/1 | 10 | 74% | 24% | 2% |
| 15 | 20/1 | 10 | 69% | 31% | 0% |

The product stream contained substantially no $CF_2=CHCl$.

EXAMPLES 16-17

The General Procedure for Fluorination was followed using 8.25 g (15 cc) of $NiCl_2/C$ (11.5% Ni) in the form of granules. The results of the reaction of HF with $CF_3CH_2Cl$ over the prepared catalyst with a 10 second contact time are given in Table 16-17.

TABLE 16-17

| Ex. | Temp. | HF/CF$_3$CH$_2$Cl | CF$_3$CH$_2$Cl | CF$_3$CH$_2$F | Other |
|-----|-------|-------------------|----------------|---------------|-------|
| 16  | 400°  | 20/1              | 99%            | 1%            | 0%    |
| 17  | 450°  | 20/1              | 98%            | 2%            | 0%    |

The product stream contained substantially no $CF_2=CHCl$.

I claim:

1. A process for the preparation of 1,1,1,2-tetrafluoroethane by fluorination of 1,1,1-trifluorochloroethane, which process comprises
    contacting in the gaseous phase at about 300° C. to about 500° C. said 1,1,1-trifluorochloroethane with HF and a catalyst comprising at least one metal,
    said metal selected from a group consisting of a metal from Groups VIII, VIIB, IIIB, IB and/or a metal having an atomic number of 58 through 71,
    said metal on aluminum fluoride or carbon,
    said metal having an oxidation state greater than zero,
    said HF and 1,1,1-trifluorochloroethane present in a mole ratio of about 3/1 to about 30/1,
    said contacting producing a product stream containing 1,1,1,2-tetrafluoroethane and, thereafter,
    separating the 1,1,1,2-tetrafluoroethane from the product stream.

2. The process of claim 1 wherein the amount of metal is about 0.02 to about 50 weight percent of the catalyst.

3. The process of claim 1 wherein the amount of metal is about 0.1 to about 10 weight percent of the catalyst.

4. The process of claim 1 wherein the HF is contacted with the 1,1,1-trifluorochloroethane at a temperature of about 300° C. to about 475° C. and a contact time of about 0.1 to about 60 seconds.

5. The process of claim 4 wherein the HF is contacted with the 1,1,1-trifluorochloroethane at a mol ratio of about 3/1 to about 20/1, at a temperature of about 350° C. to about 475° C., and a contact time of about 10 to about 30 seconds.

6. The process of claim 1 wherein the HF is contacted with the 1,1,1-trifluorochloroethane at a mol ratio of about 5/1 to about 10/1, at a temperature of about 400° C. to about 450° C., and a contact time of about 10 to about 30 seconds.

7. The process of claim 1 wherein the metal is selected from the group consisting of cobalt, lanthanum, nickel, manganese and ruthenium.

8. The process of claim 7 wherein the metal is cobalt.

9. The process of claim 7 wherein the metal is ruthenium.

10. The process of claim 7 wherein the metal is nickel.

11. The process of claim 7 wherein the metal is lanthanum.

12. The process of claim 7 wherein the metal is manganese.

13. The process of claim 1 wherein the metal is supported on carbon and the product stream contains substantially no $CF_2=CHCl$.

* * * * *